(12) United States Patent
Wlodarski et al.

(10) Patent No.: US 6,597,455 B1
(45) Date of Patent: Jul. 22, 2003

(54) FAULT DETECTION APPARATUS

(75) Inventors: Wojciech Wlodarski, North Caulfield (AU); Hatim Abdul Hamid, North Altona (AU); Alexander Zylewicz, Glenroy (AU); Sergio A Stefani, Hawthorn (AU)

(73) Assignee: CRC for Intelligent Manufacturing Systems and Technologies Ltd., Victoria (AU)

( * ) Notice: Subject to any disclaimer, the term of this patent is extended or adjusted under 35 U.S.C. 154(b) by 0 days.

(21) Appl. No.: 09/581,788
(22) PCT Filed: Apr. 19, 1999
(86) PCT No.: PCT/AU99/00291
§ 371 (c)(1),
(2), (4) Date: Aug. 11, 2000
(87) PCT Pub. No.: WO99/54715
PCT Pub. Date: Oct. 28, 1999

(30) Foreign Application Priority Data

Apr. 17, 1998 (AU) .............................................. PP2986

(51) Int. Cl.⁷ .............................................. G01N 21/84
(52) U.S. Cl. .................. 356/430; 356/237.1; 356/237.2
(58) Field of Search .............................. 356/430, 237.1, 356/237.2, 445

(56) References Cited

U.S. PATENT DOCUMENTS

| | | | | |
|---|---|---|---|---|
| 3,888,718 A | | 6/1975 | Arnaudin, Jr. et al. | |
| 4,139,306 A | * | 2/1979 | Norton | 348/131 |
| 4,317,633 A | * | 3/1982 | Kobayashi et al. | 356/601 |
| 4,358,202 A | | 11/1982 | Puffer et al. | |
| 4,563,095 A | * | 1/1986 | Puffer | 356/430 |
| 4,635,111 A | | 1/1987 | Moore | |

FOREIGN PATENT DOCUMENTS

| | | |
|---|---|---|
| DE | 3309629 | 9/1984 |
| DE | 198 01 783 A1 | 7/1999 |
| EP | 0 373 796 A3 | 6/1990 |
| EP | 0 373 796 A2 | 9/1990 |
| GB | 1 390 278 A | 4/1975 |

OTHER PUBLICATIONS

Patent Abstracrt of JP, 08147467; Sekisui Chem. Co. Ltd. Jun. 7, 1996.

* cited by examiner

Primary Examiner—Frank G. Font
Assistant Examiner—Roy M Punnoose
(74) Attorney, Agent, or Firm—Larson & Taylor, PLC

(57) ABSTRACT

Apparatus (20) for detecting faults in the exterior surface of elongate material especially enamel coated wire (W). The apparatus (20) comprises an optical head (22) through which the material (W) passes, the optical head (22) including means (35) to emit light onto the material; means (45) to collect reflected light from the material and means to monitor changes in the reflected light to indicate the presence of faults. A computer (60) is used to record the faults, their characteristics and position on a length of the material.

15 Claims, 5 Drawing Sheets

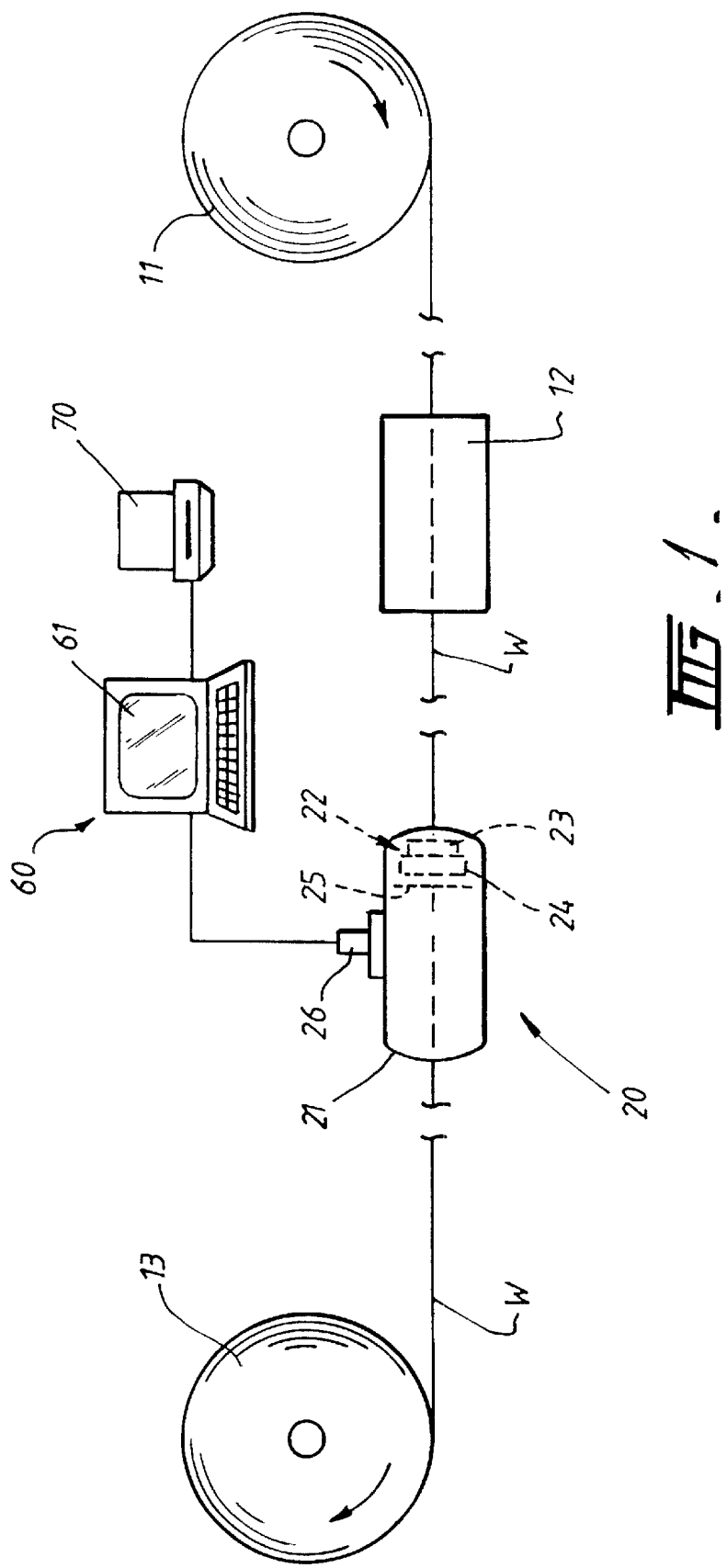

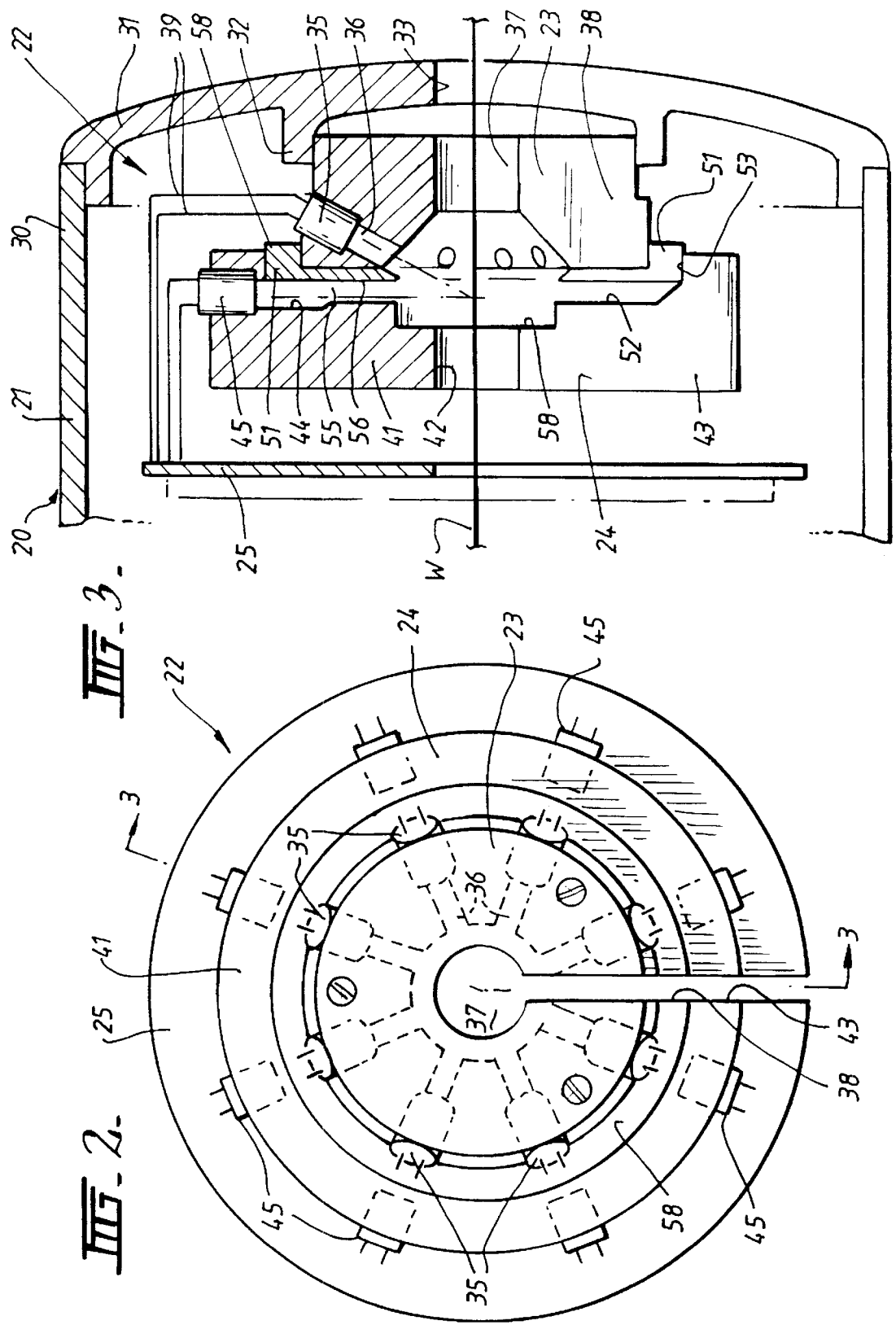

FAULT DETECTION APPARATUS

FIELD OF THE INVENTION

This invention relates to an apparatus for detecting faults during the manufacturing of elongate material. In particular the apparatus is designed to detect faults that may occur during the manufacture of coated wire and cable including optical fibre cable.

DISCUSSION OF THE ART

Enamel coated wire is used extensively in the windings of electric motors and transformers. This wire ranges from a very fine diameter of 0.019 mm to a thicker diameter of 4.7 mm.

The wire is produced at high speed in great lengths, and for instance, a drum of wire can weigh half a tonne and include 800 km of wire. The known machinery that is used to manufacture this wire, whilst it has been efficient, is not perfect and there is often an occurrence of faults or defects in the wire. Faults or defects include:

Blisters

Bare patches

Pin holes

Rippling

Enamel depth inconsistency

Curing variation (by colour)

Eccentricity of wire in enamel

Ovality of the wire and enamel

Absolute dimensions of wire and enamel

It is extremely difficult to detect the existence of faults in the wire and often these faults are only detected when the wire is in its end use. Faulty windings in an electric motor or transformer can be very dangerous and it is thus agreed by the industry that there is a need to detect faults in the wire during the production process so that for any finished spool of wire there can be an indication of the existence of faults, the characteristic of the faults and the position of faults along the length of wire as wound on the spool.

It is these problems and their solution that has brought about the present invention.

SUMMARY OF THE INVENTION

According to one aspect of the present invention there is provided apparatus for detecting faults in the exterior surface of elongate material comprising an optical head through which the material passes, the optical head including means to emit light onto the material, means to collect reflected light from the material and means to monitor changes in the reflected light to indicate the presence of faults.

In one embodiment the means to emit light comprises light sources positioned around the material in a first single plane and the means to collect light comprises receivers positioned around the material in a second single plane.

Preferably the light sources transmit light to the material at a specific angle, and the means to collect light are positioned off the line of specular reflection. Specifically the incident angle of the light is 65° to the axis of the material, and the means to collect light are at an angle of 90° to the axis of the material.

In a preferred embodiment the receivers are mounted around a body with a central light absorbing chamber, the chamber absorbing light not reflected by the material. The means to monitor changes may comprise analogue circuitry to provide an electrical signal, means to amplify and filter the signal, the signal being passed to a processor that can monitor abrupt changes in the signal and characterise the changes and the timing of the changes using digital means.

In a second embodiment the means to emit light comprises at least two coloured light sources positioned around the material in a single plane and means to collect reflected light arranged in the same single plane. Preferably, the means to collect light monitors the change in colour intensity of the reflected light.

In accordance with a further aspect of the present invention there is provided a method of detecting faults in the exterior surface of elongate material comprising passing the material through an optical head, transmitting a light signal to the material, collecting the reflected light and monitoring the reflected light to provide an indication of the existence of a fault in the exterior surface of the material.

The present invention has an objective the provision of a piece of apparatus that can be placed at the end of the production line that will monitor the wire before it is wound up onto the take-up spool. The apparatus will view the wire as it passes and monitor the existence of faults including characteristics of the type of fault, whilst at the same time record where the fault is along the length of the wire. The apparatus will use a computer to monitor and record these parameters. The invention aims to provide a comparatively simply yet effective means of monitoring faults which can be adapted to be used within existing production lines and will thus provide the manufacturers of wire of this kind with a ready indication of the state and quality and characteristics of each spool of wire.

DESCRIPTION OF THE DRAWINGS

An embodiment of the present invention will now be described by way of example only with reference to the accompanying drawings in which:

FIG. 1 is a schematic illustration of a production line for the manufacture of enamel coated wire;

FIG. 2 is an end elevation view of an optical head of apparatus for detecting faults in the wire during the production of the wire;

FIG. 3 is a cross-sectional view of a head taken along the lines 3—3 of FIG. 2.

DESCRIPTION OF THE PREFERRED EMBODIMENT

Figure 4:
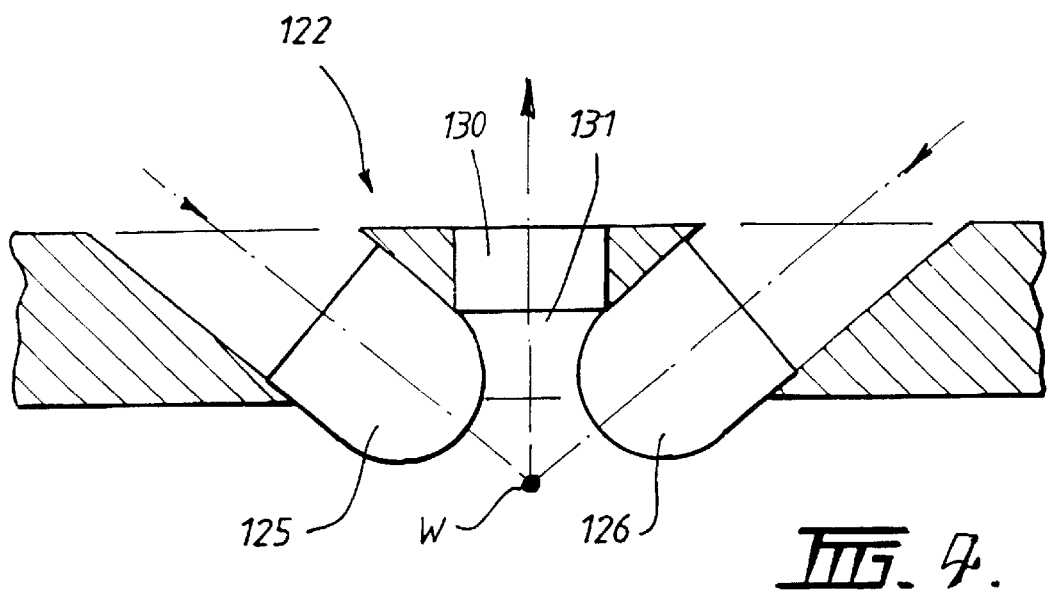
FIG. 4 is an illustration of an optical head for detecting colour variation during production of the wire.

FIG. 1 is a schematic illustration of a process line for the production of enamel coated wire. This wire is used in the windings of electric motors and transformers and varies in diameter from about 0.019 mm to 4.7 mm. The process line described herein relates to a line for producing wire of 0.27 mm diameter coated in enamel and manufactured at a process speed of 280 m per minute. It is however understood that the apparatus could be used at greater process speeds and on different wire diameter.

The wire is fed from a spool 11 to be passed through a coating station 12 to be taken up on a take-up spool 13. Each take up spool can hold approximately 50 km of wire.

The apparatus that is the subject of this invention comprises a fault detector 20 which is adapted to be placed in the production line downstream of the coating station and before the take up spool, the fault detector is coupled via a computer 60 to a screen 61 and/or printer 70 to provide both visual and hard copy information on the presence of faults in the wire.

As shown in greater detail in FIGS. 2 and 3 the fault detector 20 comprises in essence a black body outer housing 21 that supports an optical head 22 in the form of an emitter ring 23, receiver ring 24 and associated circuit board 25. The circuit board is wired to the exterior of the housing through outlet 26 which is then connected to process circuitry associated with the computer 50.

The housing is a substantially cylindrical body 30 with arcuate end plates 31, 32. The interior of the cylindrical body and ends are encoated to define a matt black finish that is resistant to electromagnetic interference. The cylindrical body 30, closed at both ends, has a narrow aperture 33, 34 at both ends defining an axial throughway. The body 30 is also provided with a radial slit (not shown) along the length and across the ends 31, 32 allowing the body to be positioned over and around a strand of wire W. A suitable stand or support mechanism is used to hold the body in a fixed position about the wire with the wire extending axially through the centre of the body. The arcuate end plate 31 of the housing clips into the cylindrical wall and has a circular boss 32 which engages, locates and positions the emitter ring 23 on the wire W. The exterior of one end of the emitter ring 23 is a force fit within the boss 32.

The optical head 22 namely the emitter ring 23, receiver ring 24 and circuit board 25 are also provided with radial slits 38, 43 and central co-axial apertures 37, 42 which allows the head to also be positioned on the wire with the wire extending axially through the head. The apertures in the housing and optical head are such that the wire can be drawn through the detector without contacting components of the fault detector.

The black body of the housing is designed to reduce ambient light. The emitter ring 23 is in the form of a first metallic annular member with a central aperture 37 that has eight equally spaced infra red light emitters 35 positioned around its circumference. Each emitter transmits infra-red light. Each emitter is positioned in an elongate passageway 36 that defines an angle of 65° to the central axis of the ring. The ring 23 also includes a radial slit 38 that facilitates location of the wire W centrally of the central aperture 37 of the ring 23. The radial extremities of the passageways 36 that house the infra-red emitters 35 provide suitable access for the wiring 39 of each emitter. The emitter ring 23 is positioned on the upstream side of the head 22 and each infra-red emitter 35 provides a light beam that projects onto the wire W as it passes through the emitter ring 23. The light projects onto the wire W with an incident angle of 65° to the axis of the wire or horizontal. The incident angle can range between 90° and 45° to the horizontal. The larger diameter receiver ring 24 is secured to the emitter ring on the downstream side and is also in the form of an annular member 41 with a central circular aperture 42 and a radially slit 43 to enable the wire W to be positioned centrally of the ring 24. The receiver ring 24 has eight equally spaced radially extending passageways 44 that house optical receivers 45. These passageways 44 are arranged at 90° to the axis of the wire. The receiver ring 24 is a two part component comprising the annular member 41 that has the radial passageways 44 and supports the optical receivers 45 and a cover plate 51 that is secured to one side of the annular member 41 that has a recessed chamber 52 of circular cross section that terminates in an annular shoulder 53 that is adjacent the periphery of the member 41. The plate 51 is screwed against the end of the shoulder 53 to define a narrow annular gap 55 between the end face of the recess and the inner surface 56 of the plate 51. This narrow gap 55 which is approximately 1 mm in width restricts passage of light reflected back from the wire to the receivers 45. The exterior of the plate 51 has an annular flange 58 that clips onto the exterior of the inner end of the emitter ring 23. The emitters and receivers are, in a preferred embodiment spaced away from the wire W at a distance of 2.5 cm. Conventional infra-red 5 mm light emitting diodes (LED) are used as the emitters. The LEDs have a blue transparent lens and a forward current of 50 mA a peak forward current of 1.2 A and power dissipation of 100 mW with a reverse voltage of 5V. The receivers are 5 mm photodiodes with a clear transparent lens.

The recess 52 terminates in the chamber 58 that surrounds the central aperture 42 through which the wire W passes. The chamber 58 has a matt black finish to absorb light that is not reflected back from the wire and picked up by the receivers. Consequently the light from the eight emitters 35 that passes the wire and is not reflected back is absorbed within the black chamber 58. The reflected light is controlled by the narrow gap 55 so that the light reflected by a single defect is viewed by the receivers 45 progressively as the wire passes through the optical head 22 and not as a single signal. The progressive view of a fault is dependent on the speed of the wire and the speed at which the receivers 45 can pick up reflected signals.

Each receiver is in the form of a phototransistor or photodiode that receives signals within a narrow waveband.

The outputs of the receivers 45 are wired to the printed circuit board 25 that is mounted on the downstream extremity of the optical head 22. The circuit board 25 is, in turn wired to the exterior of the fault detector 20 through the outlet 26. The circuitry associated with the optical head 22 has the effect of amplifying, filtering and comparing the information so that background noise caused by vibration and dust etc. can be eliminated from calculation considerations. The threshold settings can be adjusted dependent on the quality of the wire to ensure that the computer only picks up true defects. An analogue to digital converter digitises the waveform and pulses are monitored as faults.

The eight emitters are positioned so that the arcs of light overlap and they are mounted in a single plane so that the whole circumference of the wire W receives the light. The eight receivers 45 then pick up the reflected signals from the eight emitters 35 in a single plane. Although eight is the preferred number of emitters and receivers it is understood that the apparatus also works with a lower number of emitters and receivers such as four or six.

It should be noted that the receivers are not on the angle of specular reflection but are at 90° to the horizontal some 25° off the line of specular reflection. Thus, in a faultless situation most of the reflected light is not picked up by the receivers. However a defect changes the angle of reflection causing a combination of reflected and scattered light to be picked up by the receivers. This arrangement allows the apparatus to effectively accommodate vibration of the wire and also provides a very effective signal to noise ratio.

In a faultless situation the majority of the light signals that are reflected back from the wire are not picked up by the receivers and only a small uniform background signal is received as the wire travels past the head. The associated circuitry can convert the signals into a voltage which presents a substantially straight base line on a graph of voltage against time. The fineness of the wire and its speed of travel causes a degree of vibration which together with other ancillary matters such as dust cause background noise, resulting in small fluctuations in the base line that represents the collected signal of a faultless wire specimen. However, when a fault passes the optical head, the reflected signal is quite different which means that there is a substantial change in the voltage resulting in a sharp step in the output.

The associated circuitry also includes an automatic noise compensator (ATNC) which provides for automatic tracking of the raw signal coming from the defect sensing head. The ATNC comprises a noise rectifier, which converts the incoming noise, an AC voltage into a DC voltage. The ATNC produces a DC level which is used as voltage reference for a defect signal comparator. The comparator operates by comparing the signals on inputs A and B. The ATNC serves as one input, while the other is the raw signal which comes from the defect sensing head. The output of the signal comparator is a 5 Volts pulse which represents the duration in time, of the defect passing through the defect sensing head. This time measurement gives an estimate of the size of the defect. Having achieved a noise compensated system, an automatic threshold may be implemented, allowing the user to set limits for defect sizes. This is achieved by utilising a digital to analog converter (DAC). The output of the DAC is fed into input A. This in effect allows the user to add a known voltage level to the existing ATNC DC level. This gives the user the ability to set a threshold level which controls the output of the comparator.

The height and width of this step can be monitored to determine the characteristic of the fault and since the associated computer 60 is capable of recording the passage of the wire, the computer can also determine where along any particular length of wire the fault has occurred.

FIGS. 4 to 7 illustrate an embodiment that monitors the colour variation of the enamel coated wire. The colour sensor operates by illuminating the wire from a radial direction and then using a photo-sensor to detect the intensity level of the reflected light. This embodiment also comprises an optical head 122 which may be housed within the black body housing 21 illustrated in the first embodiment. Alternatively, a separate body may be used to house the head 122. The optical head 122 is illustrated schematically in FIG. 4 and in exploded form in FIG. 5 and essentially comprises two red light emitting diodes (LED) 125 and 126 and a photodiode 130 positioned in an optical mount 128 so that the LEDs and photodiode are in a single plane around the wire W. Photodiode 130 is provided with a built-in lens and an integral amplifier (not shown). The LEDs 125, 126 and photodiode 130 are mounted in the one plane with the LEDs being positioned on either side of the photodiode 130 at an angle of incidence to the vertical of 50° The photodiode 130 is mounted perpendicular to the wire and is thus midway between two LEDs 125 and 126. The photodiode 130 is also positioned at a nominal distance of 8 mm from the wire W and the circular cross-section of the wire ensures that there is a continual reflection of the light from the LEDs 125, 126 to the photodiode 130.

Illuminating the wire with a collimated beam of light from the side and then observing the reflected light provides excellent immunity to vibration because as the wire vibrates the reflected light is fairly constant. However although vibration can be accommodated it is important that the wire is in axial alignment. Thus the colour sensor is positioned in the production line between two fixed guide wheels to ensure accurate axial alignment. The wire should also pass with 0.5 mm of the centre of the sensor.

Figure 5:
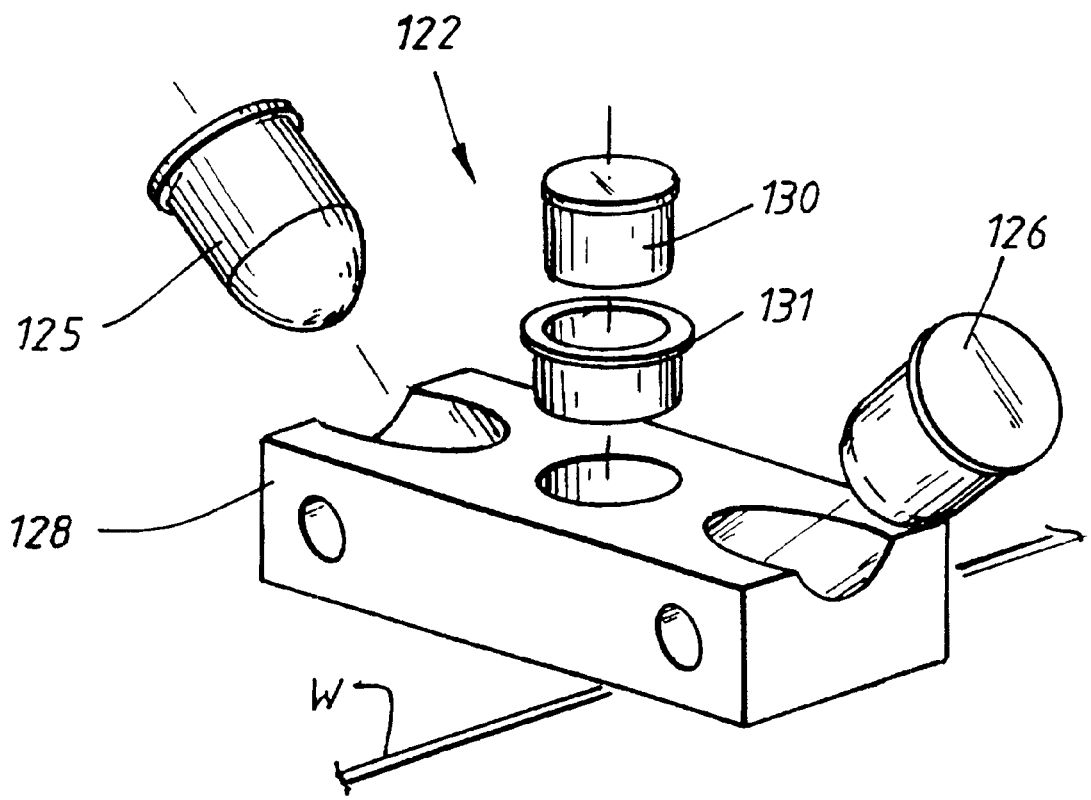
FIG. 5 is an exploded view of the optical head of FIG. 4.

As shown in FIG. 5 the photodiode 130 is mounted in a collar 131 on non conducting material to reduce the electrical noise that can be picked up by the photodiode from the metal componentry of the sensor.

Details of the LEDs 125, 126 and photodiode are:
Emitter (LED):
Colour: RED (peaking at 650 nm)
Diameter: 10 mm
Package: Untinted clear lens
Operating intensity: 4700 mcd–23000 mcd (millicandela)
View Angle: 4 Degrees
Manufacturer: Toshiba
Sensor (Photodiode with integral amplifier):
Package: TO-5 with domed lens
Frequency response: 65 kHz
Supply voltage: +−12V dc
Output: Voltage proportional to incident light level
Manufacturer: IPL (part number: IPL10530DAL)

Figure 6:
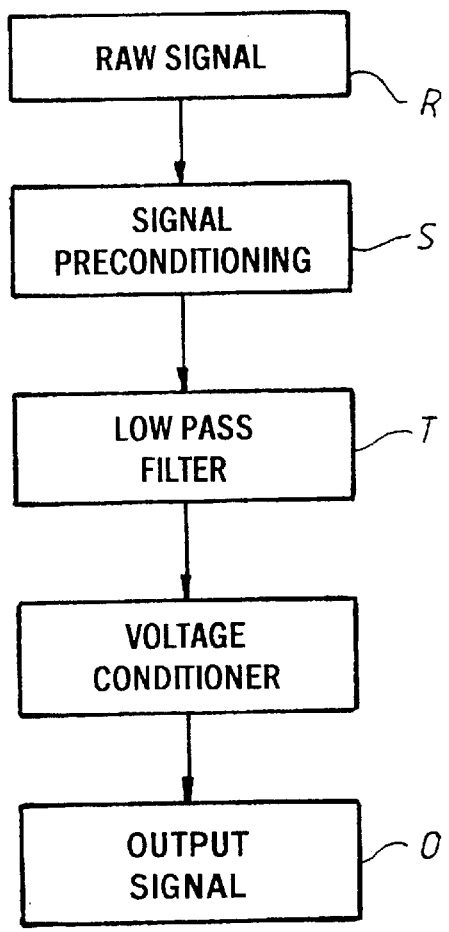
FIG. 6 is a schematic illustration of the circuitry associated with the head of FIGS. 4 and 5.

As shown in FIG. 6, the raw signal R is first amplified by the photodiode S and then in analogue form is transferred through a low pass filter T with a cut-off frequency of 0.5 Hz to suppress the effects of wire vibration and provide an output voltage O related to the colour of the enamelled wire surface. This signal is then converted to a digital value once every second by a computer with ADC capabilities. The software on the computer displays the present colour value in addition to trends over a period of two hours. All this data is then stored by the computer for future reference.

Figure 7:
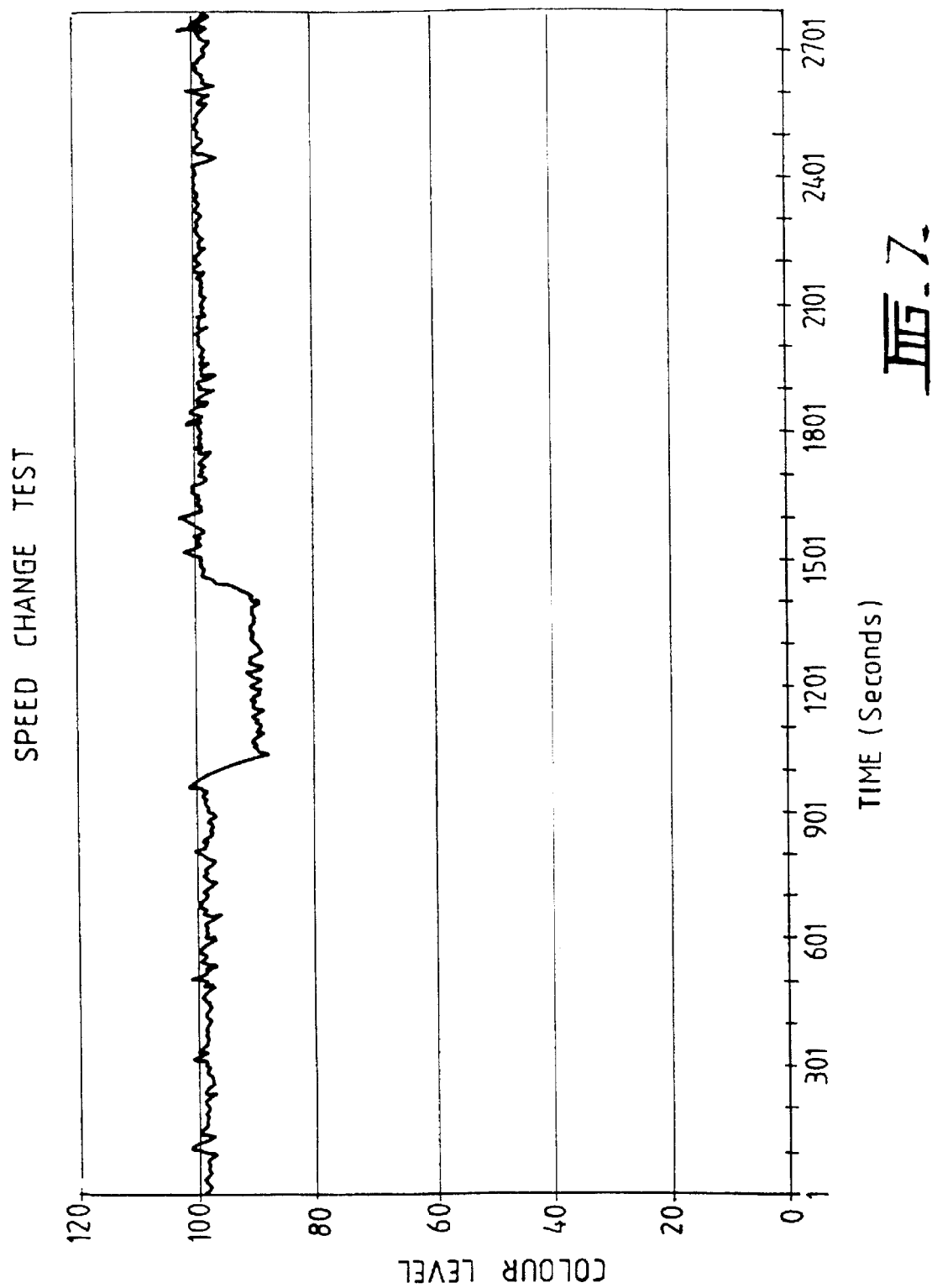
FIG. 7 is a plot of colour level against time illustrating colour variations.

FIG. 7 illustrates the sort of results that can be detected by the colour sensor. In trials, the production speed was changed by 10% which immediately produced a similar 10% change in the colour signal as illustrated by FIG. 7.

Monitoring the intensity, the colour sensor effectively examines the intensity of the red light reflected from the surface of the enamel coated wire. Any changes in the intensity provide an indication of change in enamel colour. It has been discovered that changes in colour relate to changes in insulation properties and thus the quality of the wire can be monitored based on the quality of insulation. During the production of the wire, the wire is coated and then cured in an oven. The oven temperature and the speed at which the wire passes the curing stage therefore becomes critical and monitoring the colour provides a means of optimising the curing step by ensuring maximum speed of throughput at the lowest oven temperature. In consequence, this optimisation improves the efficiency of the whole process. A further enhancement of the colour sensing apparatus described above is the provision of a feedback loop that can control speed, oven temperature and other process parameters to ensure optimum efficiency.

Consequently, through use of the apparatus, at the end of a manufacturing run, when the wire has been taken up by the take-up spool the computer 60 should have an indication of all the faults, their characteristics and position. The manufacturer of the wire can then mark the spool with this information which will determine whether the spool is of top quality, sub standard or scrap. In an extreme situation where the fault is viewed as particularly serious the computer can shut down the whole production process.

The relative positions of the emitters and receivers to the wire are selected to ensure optimum use of the light signals. It is understood that the exact parameters would vary depending on the strength of the light signals.

It is also understood that apparatus of the kind described above can be used to check for defects in other form of communication or power cable including optical fibre cable.

The apparatus described above has been designed to be added to a variety of production lines especially for the product of long lengths of enamelled wire.

What is claimed is:

1. Apparatus for detecting faults in the exterior surface of elongate material including an optical head through which the material passes, the optical head including light sources positioned around the material in a first plane to transmit light to the material at a specific angle, a plurality of receivers positioned around the material in a second plane, the receivers being positioned off the line of specular reflection, and means to monitor changes in the reflected light to indicate the presence of faults.

2. The apparatus according to claim 1 wherein the incident angle of the light is 65° to the axis of the material, and the receivers are at an angle of 90° to the axis of the material.

3. The apparatus according claim 1 wherein the light sources are mounted equally spaced around an emitter ring and the receivers are positioned equally spaced around a receiver ring, the rings being supported co-axially to define a narrow gap therebetween, the elongate material passing axially through the center of the rings.

4. The apparatus according to claim 3 wherein the centre of the rings define a central light absorbing chamber, the chamber absorbing light not reflected by the material.

5. The apparatus according to claim 1 wherein the means to emit light comprises a plurality of infra red emitters equally spaced around the material and the means to collect reflected light comprises the same number of photodiodes or phototransistors equally spaced around the material.

6. The apparatus according to claim 5 wherein each emitter produces an arc of light on the material and the edges of adjacent arcs overlap.

7. The apparatus according to claim 1 wherein the means to monitor changes comprises analogue circuitry to provide an electrical signal, means to amplify and filter the signal, the signal being passed to a processor that can monitor abrupt changes in the signal and characterise the changes and the timing of the changes using digital means.

8. The apparatus according to claim 7 wherein the processor includes a computer that can store the monitored information to provide comprehensive information on the position and characteristics of faults in a length of material.

9. Apparatus for detecting faults in the exterior surface of elongate material including an optical head through which the material passes, the optical head including means to emit light onto the material; the means to emit light comprises at least two coloured light sources positioned on opposite sides of the material in a single plane, means to collect reflected light from the material, said means being positioned in the same single plane at an angle midway between the light sources; and means to monitor changes in the reflected light to indicate the presence of faults.

10. The apparatus according to claim 9 wherein the means to collect reflected light is coupled to means to monitor the change in colour intensity of the reflected light.

11. The apparatus according to claim 10 wherein a first red LED is positioned inclined at 55° to the vertical on one side of the material and a second red LED is positioned on the opposite side of the material also at 55° to the vertical, a photodiode being positioned on the vertical to collect reflected light.

12. A method of detecting faults in the exterior surface of elongate material comprising passing the material through an optical head and whilst in the head, transmitting a light signal to the material at an incident angle, collecting only the light reflected off the line of specular reflection and monitoring the reflected light to provide an indication of the existence of a fault in the exterior surface of the material.

13. A method producing enamel coated wire comprising feeding a length of wire through a coating station to enamel coat the wire, passing the wire through an optical head and whilst in the head, transmitting a light signal to the wire at an incident angle, collecting only the light reflected off the line of specular reflection and monitoring the reflected light to provide an indication of the existence of a fault in the exterior, monitoring the occurrence, type and position of faults, and winding the coated wire onto a take up spool.

14. The method according to claim 13 comprising stopping the production in the event of the detection of a particular category of fault.

15. The method according to claim 13 comprising controlling one or more parameter associated with the production process in accordance with detection of faults.

* * * * *